US012690934B2

(12) United States Patent
Choi et al.

(10) Patent No.: US 12,690,934 B2
(45) Date of Patent: Jul. 28, 2026

(54) POSITION CONTROL FOR PATIENT CONSOLE

(71) Applicant: EndoQuest Robotics, Inc., Houston, TX (US)

(72) Inventors: Jiwon Choi, Houston, TX (US); Jeihan Lee, Houston, TX (US); Jinseok Noh, Houston, TX (US); Yangjae Kang, Houston, TX (US); Dongsuk Shin, Houston, TX (US)

(73) Assignee: EndoQuest Robotics, Inc., Houston, TX (US)

( * ) Notice: Subject to any disclaimer, the term of this patent is extended or adjusted under 35 U.S.C. 154(b) by 352 days.

(21) Appl. No.: 18/198,694

(22) Filed: May 17, 2023

(65) Prior Publication Data

US 2023/0363842 A1     Nov. 16, 2023

Related U.S. Application Data

(63) Continuation of application No. PCT/US2022/051225, filed on Nov. 29, 2022.

(60) Provisional application No. 63/284,506, filed on Nov. 30, 2021.

(51) Int. Cl.
   *A61B 34/30*     (2016.01)
   *A61B 34/00*     (2016.01)
   *A61B 34/37*     (2016.01)
(52) U.S. Cl.
   CPC .............. *A61B 34/37* (2016.02); *A61B 34/70* (2016.02)
(58) Field of Classification Search
   CPC ................................ A61B 34/37; A61B 34/70
   See application file for complete search history.

(56) References Cited

U.S. PATENT DOCUMENTS

| | | | |
|---|---|---|---|
| 5,792,135 A | 8/1998 | Madhani et al. | |
| 5,797,900 A | 8/1998 | Madhani et al. | |
| 5,976,122 A | 11/1999 | Madhani et al. | |
| 6,063,095 A | 5/2000 | Wang et al. | |
| 6,132,368 A | 10/2000 | Cooper | |
| 6,244,809 B1 | 6/2001 | Wang et al. | |
| 6,246,200 B1 | 6/2001 | Blumenkranz et al. | |

(Continued)

FOREIGN PATENT DOCUMENTS

| | | |
|---|---|---|
| CN | 105310775 A | 2/2016 |
| CN | 108309370 A | 7/2018 |

(Continued)

OTHER PUBLICATIONS

Taiwan Intellectual Property Office, Office Action dated Jun. 13, 2023, in corresponding TW Patent Application No. 111145623.

(Continued)

*Primary Examiner* — Eric D. Bertram
(74) *Attorney, Agent, or Firm* — Troutman Pepper Locke LLP; Scott D. Wofsy; Michael J. Pollack

(57) ABSTRACT

A patient console for a robotic surgical system can include a base, and a positioning assembly attached to the base and configured to position an instrument controller assembly. The positioning assembly includes a remote control device operatively connected to the positioning assembly to control movement of one or more portions of the positioning assembly such that a user is capable of having a direct line-of-sight of a patient when using the remote control device.

17 Claims, 13 Drawing Sheets

(56)                  References Cited

U.S. PATENT DOCUMENTS

| | | | |
|---|---|---|---|
| 6,312,435 | B1 | 11/2001 | Wallace et al. |
| 6,331,181 | B1 | 12/2001 | Tierney et al. |
| 6,346,072 | B1 | 2/2002 | Cooper |
| 6,364,888 | B1 | 4/2002 | Niemeyer et al. |
| 6,371,952 | B1 | 4/2002 | Madhani et al. |
| 6,394,998 | B1 | 5/2002 | Wallace et al. |
| 6,424,885 | B1 | 7/2002 | Niemeyer et al. |
| 6,441,577 | B2 | 8/2002 | Blumenkranz et al. |
| 6,451,027 | B1 | 9/2002 | Cooper et al. |
| 6,491,691 | B1 | 12/2002 | Morley et al. |
| 6,491,701 | B2 | 12/2002 | Tierney et al. |
| 6,493,608 | B1 | 12/2002 | Niemeyer |
| 6,522,906 | B1 | 2/2003 | Salisbury, Jr. et al. |
| 6,565,554 | B1 | 5/2003 | Niemeyer |
| 6,587,750 | B2 | 7/2003 | Gerbi et al. |
| 6,645,196 | B1 | 11/2003 | Nixon et al. |
| 6,671,581 | B2 | 12/2003 | Niemeyer et al. |
| 6,676,684 | B1 | 1/2004 | Morley et al. |
| 6,684,129 | B2 | 1/2004 | Salisbury, Jr. et al. |
| 6,699,177 | B1 | 3/2004 | Wang et al. |
| 6,699,235 | B2 | 3/2004 | Wallace et al. |
| 6,714,839 | B2 | 3/2004 | Salisbury, Jr. et al. |
| 6,746,443 | B1 | 6/2004 | Morley et al. |
| 6,766,204 | B2 | 7/2004 | Niemeyer et al. |
| 6,783,524 | B2 | 8/2004 | Anderson et al. |
| 6,785,593 | B2 | 8/2004 | Wang et al. |
| 6,799,088 | B2 | 9/2004 | Wang et al. |
| 6,817,972 | B2 | 11/2004 | Snow |
| 6,817,974 | B2 | 11/2004 | Cooper et al. |
| 6,836,703 | B2 | 12/2004 | Wang et al. |
| 6,837,846 | B2 | 1/2005 | Jaffe et al. |
| 6,840,938 | B1 | 1/2005 | Morley et al. |
| 6,852,107 | B2 | 2/2005 | Wang et al. |
| 6,866,671 | B2 | 3/2005 | Tierney et al. |
| 6,871,117 | B2 | 3/2005 | Wang et al. |
| 6,892,112 | B2 | 5/2005 | Wang et al. |
| 6,905,491 | B1 | 6/2005 | Wang et al. |
| 6,951,535 | B2 | 10/2005 | Ghodoussi et al. |
| 6,991,627 | B2 | 1/2006 | Madhani et al. |
| 6,994,703 | B2 | 2/2006 | Wang et al. |
| 7,025,064 | B2 | 4/2006 | Wang et al. |
| 7,027,892 | B2 | 4/2006 | Wang et al. |
| 7,048,745 | B2 | 5/2006 | Tierney et al. |
| 7,066,926 | B2 | 6/2006 | Wallace et al. |
| 7,074,179 | B2 | 7/2006 | Wang et al. |
| 7,083,571 | B2 | 8/2006 | Wang et al. |
| 7,087,049 | B2 | 8/2006 | Nowlin et al. |
| 7,090,637 | B2 | 8/2006 | Danitz et al. |
| 7,118,582 | B1 | 10/2006 | Wang et al. |
| 7,125,403 | B2 | 10/2006 | Julian et al. |
| 7,155,315 | B2 | 12/2006 | Niemeyer et al. |
| 7,204,844 | B2 | 4/2007 | Jensen et al. |
| 7,276,065 | B2 | 10/2007 | Morley et al. |
| 7,320,700 | B2 | 1/2008 | Cooper et al. |
| 7,331,967 | B2 | 2/2008 | Lee et al. |
| 7,333,642 | B2 | 2/2008 | Green |
| 7,357,774 | B2 | 4/2008 | Cooper |
| 7,398,707 | B2 | 7/2008 | Morley et al. |
| 7,524,320 | B2 | 4/2009 | Tierney et al. |
| 7,574,250 | B2 | 8/2009 | Niemeyer |
| 7,608,083 | B2 | 10/2009 | Lee et al. |
| 7,615,066 | B2 | 11/2009 | Danitz et al. |
| 7,691,098 | B2 | 4/2010 | Wallace et al. |
| 7,744,608 | B2 | 6/2010 | Lee et al. |
| 7,756,036 | B2 | 7/2010 | Druke et al. |
| 7,757,028 | B2 | 7/2010 | Druke et al. |
| 7,763,015 | B2 | 7/2010 | Cooper et al. |
| 7,780,651 | B2 | 8/2010 | Madhani et al. |
| 7,837,674 | B2 | 11/2010 | Cooper |
| 7,854,738 | B2 | 12/2010 | Lee et al. |
| 7,865,266 | B2 | 1/2011 | Moll et al. |
| 7,955,322 | B2 | 6/2011 | Devengenzo et al. |
| 8,052,636 | B2 | 11/2011 | Moll et al. |
| 8,054,752 | B2 | 11/2011 | Druke et al. |
| 8,068,649 | B2 | 11/2011 | Green |
| 8,075,474 | B2 | 12/2011 | Honda et al. |
| 8,100,133 | B2 | 1/2012 | Mintz et al. |
| 8,120,301 | B2 | 2/2012 | Goldberg et al. |
| 8,123,740 | B2 | 2/2012 | Madhani et al. |
| 8,147,503 | B2 | 4/2012 | Zhao et al. |
| 8,169,468 | B2 | 5/2012 | Scott et al. |
| 8,182,415 | B2 | 5/2012 | Larkin et al. |
| 8,190,238 | B2 | 5/2012 | Moll et al. |
| 8,228,368 | B2 | 7/2012 | Zhao et al. |
| 8,323,297 | B2 | 12/2012 | Hinman et al. |
| 8,335,590 | B2 | 12/2012 | Costa et al. |
| 8,337,521 | B2 | 12/2012 | Cooper et al. |
| 8,343,045 | B2 | 1/2013 | Swinehart et al. |
| 8,343,141 | B2 | 1/2013 | Madhani et al. |
| 8,365,633 | B2 | 2/2013 | Simaan et al. |
| 8,375,808 | B2 | 2/2013 | Blumenkranz et al. |
| 8,398,541 | B2 | 3/2013 | DiMaio et al. |
| 8,437,629 | B2 | 5/2013 | McDowall |
| 8,469,947 | B2 | 6/2013 | Devengenzo et al. |
| 8,475,366 | B2 | 7/2013 | Boulais et al. |
| 8,506,555 | B2 | 8/2013 | Ruiz Morales |
| 8,594,841 | B2 | 11/2013 | Zhao et al. |
| 8,597,280 | B2 | 12/2013 | Cooper et al. |
| 8,600,551 | B2 | 12/2013 | Itkowitz et al. |
| 8,617,102 | B2 | 12/2013 | Moll et al. |
| 8,644,988 | B2 | 2/2014 | Prisco et al. |
| 8,679,099 | B2 | 3/2014 | Cooper et al. |
| 8,690,908 | B2 | 4/2014 | Cooper et al. |
| 8,709,000 | B2 | 4/2014 | Madhani et al. |
| 8,740,885 | B2 | 6/2014 | Larkin et al. |
| 8,784,435 | B2 | 7/2014 | Cooper et al. |
| 8,786,241 | B2 | 7/2014 | Nowlin et al. |
| 8,790,243 | B2 | 7/2014 | Cooper et al. |
| 8,801,661 | B2 | 8/2014 | Moll et al. |
| 8,810,631 | B2 | 8/2014 | Scott et al. |
| 8,816,628 | B2 | 8/2014 | Nowlin et al. |
| 8,821,480 | B2 | 9/2014 | Burbank |
| 8,831,782 | B2 | 9/2014 | Itkowitz |
| 8,838,270 | B2 | 9/2014 | Druke et al. |
| 8,852,208 | B2 | 10/2014 | Gomez et al. |
| 8,887,595 | B2 | 11/2014 | Williams |
| 8,888,690 | B2 | 11/2014 | Swinehart et al. |
| 8,888,764 | B2 | 11/2014 | Devengenzo et al. |
| 8,903,549 | B2 | 12/2014 | Itkowitz et al. |
| 8,918,207 | B2 | 12/2014 | Prisco |
| 8,944,070 | B2 | 2/2015 | Guthart et al. |
| 8,945,095 | B2 | 2/2015 | Blumenkranz et al. |
| 9,011,318 | B2 | 4/2015 | Choset et al. |
| 9,050,120 | B2 | 6/2015 | Swarup et al. |
| 9,060,678 | B2 | 6/2015 | Larkin et al. |
| 9,089,354 | B2 | 7/2015 | Simaan et al. |
| 9,095,362 | B2 | 8/2015 | Dachs et al. |
| 9,138,284 | B2 | 9/2015 | Krom et al. |
| 9,144,456 | B2 | 9/2015 | Rosa et al. |
| 9,186,221 | B2 | 11/2015 | Burbank |
| 9,254,090 | B2 | 2/2016 | Watson et al. |
| 9,259,274 | B2 | 2/2016 | Prisco |
| 9,259,276 | B2 | 2/2016 | Mintz et al. |
| 9,301,807 | B2 | 4/2016 | Duval |
| 9,308,937 | B2 | 4/2016 | Griffiths et al. |
| 9,339,341 | B2 | 5/2016 | Cooper |
| 9,358,074 | B2 | 6/2016 | Schena et al. |
| 9,456,839 | B2 | 10/2016 | Cooper |
| 9,486,288 | B2 | 11/2016 | Devengenzo et al. |
| 9,498,242 | B2 | 11/2016 | Crews et al. |
| 9,504,517 | B2 | 11/2016 | Rosa et al. |
| 9,510,915 | B2 | 12/2016 | Madhani et al. |
| 9,565,990 | B2 | 2/2017 | Lee et al. |
| 9,687,310 | B2 | 6/2017 | Nowlin et al. |
| 9,717,486 | B2 | 8/2017 | Cooper et al. |
| 9,757,149 | B2 | 9/2017 | Cooper et al. |
| 9,757,203 | B2 | 9/2017 | Hourtash et al. |
| 9,775,678 | B2 | 10/2017 | Lohmeier |
| 9,782,056 | B2 | 10/2017 | McDowall |
| 9,782,225 | B2 | 10/2017 | Lohmeier et al. |
| 9,795,446 | B2 | 10/2017 | DiMaio et al. |
| 9,795,453 | B2 | 10/2017 | Tierney et al. |
| 9,801,526 | B2 | 10/2017 | Larkin et al. |
| 9,801,654 | B2 | 10/2017 | Gomez et al. |

(56)  References Cited

U.S. PATENT DOCUMENTS

| | | |
|---|---|---|
| 9,814,527 B2 | 11/2017 | Rogers et al. |
| 9,877,794 B2 | 1/2018 | Csiky |
| 9,901,402 B2 | 2/2018 | Itkowitz et al. |
| 9,918,659 B2 | 3/2018 | Chopra et al. |
| 9,949,620 B2 | 4/2018 | Duval et al. |
| 9,962,066 B2 | 5/2018 | Rogers et al. |
| 9,968,405 B2 | 5/2018 | Cooper et al. |
| 9,980,630 B2 | 5/2018 | Larkin et al. |
| 10,010,331 B2 | 7/2018 | Morash |
| 10,039,473 B2 | 8/2018 | Zhao et al. |
| 10,058,390 B2 | 8/2018 | Simaan et al. |
| 10,085,788 B2 | 10/2018 | Privitera et al. |
| 10,085,806 B2 | 10/2018 | Hagn et al. |
| 10,092,172 B2 | 10/2018 | Peh et al. |
| 10,105,128 B2 | 10/2018 | Cooper et al. |
| 10,117,715 B2 | 11/2018 | Lohmeier et al. |
| 10,159,536 B2 | 12/2018 | Kralicky et al. |
| 10,178,368 B2 | 1/2019 | Zhao et al. |
| 10,179,024 B2 | 1/2019 | Yeung |
| 10,179,413 B2 | 1/2019 | Rockrohr |
| 10,188,472 B2 | 1/2019 | Diolaiti et al. |
| 10,258,421 B2 | 4/2019 | Lohmeier et al. |
| 10,278,782 B2 | 5/2019 | Jarc et al. |
| 10,321,964 B2 | 6/2019 | Grover et al. |
| 10,327,856 B2 | 6/2019 | Kralicky et al. |
| 10,363,107 B2 * | 7/2019 | Blumenkranz ........ A61B 90/98 |
| 10,365,295 B2 | 7/2019 | Blumenkranz et al. |
| 10,390,687 B2 | 8/2019 | Choi et al. |
| 10,390,895 B2 | 8/2019 | Henderson et al. |
| 10,391,635 B2 | 8/2019 | Berghofer et al. |
| 10,398,520 B2 | 9/2019 | Larkin et al. |
| 10,413,370 B2 | 9/2019 | Yates et al. |
| 10,448,813 B2 | 10/2019 | Cooper et al. |
| 10,456,166 B2 | 10/2019 | Cooper et al. |
| 10,507,068 B2 | 12/2019 | Kopp et al. |
| 10,512,481 B2 | 12/2019 | Cooper |
| 10,524,644 B2 | 1/2020 | Scott et al. |
| 10,524,868 B2 | 1/2020 | Cooper et al. |
| 10,531,929 B2 | 1/2020 | Widenhouse et al. |
| 10,602,958 B2 | 3/2020 | Silverstein et al. |
| 10,646,990 B2 | 5/2020 | Olds et al. |
| 10,660,713 B2 | 5/2020 | McCrea et al. |
| 10,682,193 B2 | 6/2020 | Choi et al. |
| 10,729,503 B2 | 8/2020 | Cameron |
| 10,736,702 B2 | 8/2020 | Harris et al. |
| 10,779,896 B2 | 9/2020 | Dachs, II et al. |
| 10,779,899 B2 | 9/2020 | Griffiths et al. |
| 10,786,329 B2 | 9/2020 | Schuh et al. |
| 10,820,953 B2 | 11/2020 | Kralicky et al. |
| 10,828,115 B2 | 11/2020 | Koenig et al. |
| 10,828,117 B2 | 11/2020 | Evans |
| 10,835,331 B2 | 11/2020 | Burbank |
| 10,835,335 B2 | 11/2020 | Perdue et al. |
| 10,856,946 B2 | 12/2020 | Solomon et al. |
| 10,864,051 B2 | 12/2020 | Simi et al. |
| 10,874,475 B2 | 12/2020 | Iceman |
| 10,898,189 B2 | 1/2021 | McDonald, II |
| 10,898,281 B2 | 1/2021 | Cooper et al. |
| 10,905,505 B1 | 2/2021 | Barakat et al. |
| 10,918,449 B2 | 2/2021 | Solomon et al. |
| 10,939,970 B2 | 3/2021 | Laakso et al. |
| 10,959,607 B2 | 3/2021 | Rogers et al. |
| 2002/0161281 A1 | 10/2002 | Jaffe et al. |
| 2003/0036748 A1 | 2/2003 | Cooper et al. |
| 2003/0083673 A1 | 5/2003 | Tierney et al. |
| 2003/0114962 A1 | 6/2003 | Niemeyer |
| 2003/0135203 A1 | 7/2003 | Wang et al. |
| 2004/0049205 A1 | 3/2004 | Lee et al. |
| 2004/0138700 A1 | 7/2004 | Cooper et al. |
| 2004/0162547 A1 | 8/2004 | Wallace et al. |
| 2004/0236316 A1 | 11/2004 | Danitz et al. |
| 2005/0043718 A1 | 2/2005 | Madhani et al. |
| 2005/0059960 A1 | 3/2005 | Simaan et al. |
| 2005/0149003 A1 | 7/2005 | Tierney et al. |
| 2005/0200324 A1 | 9/2005 | Guthart et al. |

| | | |
|---|---|---|
| 2005/0204851 A1 | 9/2005 | Morley et al. |
| 2005/0216033 A1 | 9/2005 | Lee et al. |
| 2005/0251112 A1 | 11/2005 | Danitz et al. |
| 2006/0167440 A1 | 7/2006 | Cooper et al. |
| 2007/0018958 A1 | 1/2007 | Tavakoli et al. |
| 2007/0043338 A1 | 2/2007 | Moll et al. |
| 2007/0137372 A1 | 6/2007 | Devengenzo et al. |
| 2007/0151390 A1 | 7/2007 | Blumenkranz et al. |
| 2007/0156119 A1 | 7/2007 | Wallace et al. |
| 2007/0156122 A1 | 7/2007 | Cooper |
| 2007/0197896 A1 | 8/2007 | Moll et al. |
| 2007/0299427 A1 * | 12/2007 | Yeung ................... A61B 34/77 606/1 |
| 2008/0065105 A1 | 3/2008 | Larkin et al. |
| 2008/0065107 A1 | 3/2008 | Larkin et al. |
| 2008/0065111 A1 * | 3/2008 | Blumenkranz ...... B25J 15/0009 606/130 |
| 2008/0071291 A1 | 3/2008 | Duval et al. |
| 2008/0077159 A1 | 3/2008 | Madhani et al. |
| 2008/0177282 A1 | 7/2008 | Lee et al. |
| 2008/0177284 A1 | 7/2008 | Lee et al. |
| 2008/0287963 A1 | 11/2008 | Rogers et al. |
| 2009/0023989 A1 | 1/2009 | Honda et al. |
| 2009/0171151 A1 | 7/2009 | Choset et al. |
| 2010/0011901 A1 | 1/2010 | Burbank |
| 2010/0048999 A1 | 2/2010 | Boulais et al. |
| 2010/0082041 A1 | 4/2010 | Prisco |
| 2010/0234831 A1 | 9/2010 | Hinman et al. |
| 2010/0274087 A1 | 10/2010 | Diolaiti et al. |
| 2010/0292708 A1 | 11/2010 | Madhani et al. |
| 2011/0118755 A1 | 5/2011 | Cooper et al. |
| 2011/0125166 A1 | 5/2011 | Cooper et al. |
| 2011/0144658 A1 | 6/2011 | Wenderow et al. |
| 2011/0152879 A1 | 6/2011 | Williams |
| 2011/0196419 A1 | 8/2011 | Cooper |
| 2011/0277580 A1 | 11/2011 | Cooper et al. |
| 2011/0282351 A1 | 11/2011 | Cooper et al. |
| 2011/0282359 A1 | 11/2011 | Duval |
| 2011/0282491 A1 | 11/2011 | Prisco et al. |
| 2011/0288561 A1 | 11/2011 | Devengenzo et al. |
| 2011/0313449 A1 | 12/2011 | Cooper |
| 2012/0071895 A1 * | 3/2012 | Stahler ................... A61B 34/35 606/130 |
| 2012/0150192 A1 | 6/2012 | Dachs, II et al. |
| 2012/0203271 A1 | 8/2012 | Larkin et al. |
| 2012/0209174 A1 | 8/2012 | Moll et al. |
| 2012/0221011 A1 | 8/2012 | Larkin et al. |
| 2012/0232339 A1 | 9/2012 | Csiky |
| 2013/0041368 A1 * | 2/2013 | Cunningham ......... A61B 34/30 606/34 |
| 2013/0053868 A1 | 2/2013 | Cooper et al. |
| 2013/0079794 A9 | 3/2013 | Cooper et al. |
| 2013/0096540 A1 | 4/2013 | Cooper et al. |
| 2013/0110131 A1 | 5/2013 | Madhani et al. |
| 2013/0197539 A1 | 8/2013 | Simaan et al. |
| 2013/0197540 A1 | 8/2013 | Simaan et al. |
| 2013/0267950 A1 | 10/2013 | Rosa et al. |
| 2013/0267964 A1 | 10/2013 | Rogers et al. |
| 2013/0274761 A1 | 10/2013 | Devengenzo et al. |
| 2013/0282173 A1 * | 10/2013 | Gunday ................. A61B 34/72 901/30 |
| 2014/0081292 A1 | 3/2014 | Moll et al. |
| 2014/0194899 A1 | 7/2014 | Madhani et al. |
| 2014/0243852 A1 | 8/2014 | Cooper et al. |
| 2014/0257336 A1 | 9/2014 | Choi et al. |
| 2014/0277106 A1 | 9/2014 | Crews et al. |
| 2014/0296637 A1 | 10/2014 | Lee et al. |
| 2014/0296872 A1 | 10/2014 | Cooper et al. |
| 2015/0066002 A1 | 3/2015 | Cooper et al. |
| 2015/0150636 A1 | 6/2015 | Hagn et al. |
| 2015/0173726 A1 | 6/2015 | Lohmeier et al. |
| 2015/0173729 A1 | 6/2015 | Lohmeier et al. |
| 2015/0173731 A1 | 6/2015 | Lohmeier et al. |
| 2015/0173840 A1 | 6/2015 | Lohmeier |
| 2015/0238267 A1 | 8/2015 | Devengenzo et al. |
| 2015/0250546 A1 | 9/2015 | Larkin et al. |
| 2016/0015447 A1 | 1/2016 | Rosa et al. |
| 2016/0058512 A1 | 3/2016 | Gomez et al. |
| 2016/0066773 A1 | 3/2016 | Cooper et al. |

(56) References Cited

U.S. PATENT DOCUMENTS

| | | |
|---|---|---|
| 2016/0242860 A1 | 8/2016 | Diolaiti et al. |
| 2016/0256183 A1 | 9/2016 | Cooper |
| 2017/0014197 A1 | 1/2017 | McCrea et al. |
| 2017/0020615 A1 | 1/2017 | Koenig et al. |
| 2017/0071628 A1 | 3/2017 | Cooper et al. |
| 2017/0112505 A1 | 4/2017 | Morash |
| 2017/0156804 A1 | 6/2017 | Cooper et al. |
| 2017/0265923 A1 | 9/2017 | Privitera et al. |
| 2017/0266357 A1 | 9/2017 | Douglas et al. |
| 2017/0273749 A1 | 9/2017 | Grover et al. |
| 2017/0274533 A1 | 9/2017 | Berghofer et al. |
| 2017/0281296 A1 | 10/2017 | Cooper et al. |
| 2017/0308667 A1 | 10/2017 | Beira et al. |
| 2017/0312043 A1 | 11/2017 | Ogawa et al. |
| 2017/0325879 A1 | 11/2017 | Yeung |
| 2017/0354318 A1 | 12/2017 | Rogers et al. |
| 2017/0367775 A1 | 12/2017 | Dachs, II et al. |
| 2017/0367777 A1 | 12/2017 | Kralicky et al. |
| 2018/0000318 A9 | 1/2018 | Rogers et al. |
| 2018/0000548 A1 | 1/2018 | Olds et al. |
| 2018/0014852 A1 | 1/2018 | Gomez et al. |
| 2018/0049820 A1 | 2/2018 | Widenhouse et al. |
| 2018/0049822 A1 | 2/2018 | Henderson et al. |
| 2018/0049827 A1 | 2/2018 | Harris et al. |
| 2018/0064498 A1 | 3/2018 | Kapadia et al. |
| 2018/0111273 A1 | 4/2018 | Linnell et al. |
| 2018/0132956 A1 | 5/2018 | Cameron |
| 2018/0168747 A1 | 6/2018 | Kopp et al. |
| 2018/0168752 A1 | 6/2018 | Scheib et al. |
| 2018/0193007 A1 | 7/2018 | Au et al. |
| 2018/0200894 A1 | 7/2018 | Rockrohr |
| 2018/0214176 A1 | 8/2018 | Solomon et al. |
| 2018/0221096 A1 | 8/2018 | Yates et al. |
| 2018/0242824 A1 | 8/2018 | Larkin et al. |
| 2018/0256270 A1 | 9/2018 | Cooper et al. |
| 2018/0271607 A1 | 9/2018 | Kralicky et al. |
| 2018/0271616 A1 | 9/2018 | Schuh et al. |
| 2018/0286287 A1 | 10/2018 | Razzaque |
| 2018/0296299 A1 | 10/2018 | Iceman |
| 2018/0317915 A1 | 11/2018 | Mcdonald, II |
| 2018/0318023 A1 | 11/2018 | Griffiths et al. |
| 2018/0353204 A1 | 12/2018 | Solomon et al. |
| 2018/0370045 A1 | 12/2018 | Kan |
| 2019/0039241 A1 | 2/2019 | Langenfeld et al. |
| 2019/0117318 A1* | 4/2019 | Charron ............... A61B 5/0077 |
| 2019/0125467 A1 | 5/2019 | Evans |
| 2019/0216551 A1 | 7/2019 | Burbank |
| 2019/0269472 A1 | 9/2019 | Kralicky et al. |
| 2019/0274769 A1 | 9/2019 | Perdue et al. |
| 2019/0298160 A1* | 10/2019 | Ummalaneni ... A61B 1/000094 |
| 2019/0328472 A1 | 10/2019 | Tojo et al. |
| 2019/0380801 A1* | 12/2019 | Savall ..................... A61B 34/20 |
| 2020/0019205 A1* | 1/2020 | Cuthbertson .......... G05G 9/047 |
| 2020/0038123 A1 | 2/2020 | Graetzel et al. |
| 2020/0069389 A1 | 3/2020 | Morrissette et al. |
| 2020/0146763 A1 | 5/2020 | Schena et al. |
| 2020/0179067 A1* | 6/2020 | Ross ..................... A61B 34/30 |
| 2020/0205917 A1 | 7/2020 | Peine et al. |
| 2020/0214774 A1 | 7/2020 | Yoshida et al. |
| 2020/0297444 A1 | 9/2020 | Camarillo et al. |
| 2020/0330173 A1 | 10/2020 | Kapadia et al. |
| 2020/0367979 A1 | 11/2020 | Laakso et al. |
| 2020/0397456 A1 | 12/2020 | Kim et al. |
| 2021/0045819 A1 | 2/2021 | Castillo et al. |
| 2021/0052258 A1 | 2/2021 | Mortazavi Moghadam et al. |
| 2021/0121253 A1 | 4/2021 | Leibrandt |
| 2021/0169605 A1 | 6/2021 | Calloway et al. |
| 2021/0241542 A1 | 8/2021 | Shmayahu et al. |
| 2021/0259794 A1 | 8/2021 | Kato et al. |
| 2021/0267702 A1 | 9/2021 | Kim et al. |
| 2021/0275266 A1 | 9/2021 | Kim et al. |
| 2021/0338052 A1 | 11/2021 | Ouyang et al. |
| 2022/0354524 A1 | 11/2022 | Kim et al. |
| 2023/0210618 A1 | 7/2023 | Kim et al. |
| 2023/0210621 A1 | 7/2023 | Noh et al. |
| 2023/0248419 A1 | 8/2023 | Cho et al. |
| 2023/0248450 A1 | 8/2023 | Ravi et al. |
| 2023/0248457 A1 | 8/2023 | Lee et al. |
| 2023/0255702 A1 | 8/2023 | Park et al. |
| 2023/0285090 A1 | 9/2023 | Lee et al. |
| 2023/0285098 A1 | 9/2023 | Lee et al. |
| 2023/0285099 A1 | 9/2023 | Lee et al. |
| 2023/0355221 A1 | 11/2023 | Shin et al. |
| 2023/0363847 A1 | 11/2023 | Lee et al. |
| 2023/0398680 A1* | 12/2023 | Park .................... A61B 90/361 |
| 2024/0058079 A1 | 2/2024 | Kim et al. |

FOREIGN PATENT DOCUMENTS

| | | |
|---|---|---|
| CN | 108472097 A | 8/2018 |
| CN | 109674647 A | 4/2019 |
| CN | 213606867 U | 7/2021 |
| EP | 2968048 B1 | 6/2018 |
| EP | 3175813 B1 | 1/2020 |
| JP | 2019530517 A | 10/2019 |
| JP | 2020104843 A | 7/2020 |
| JP | 2021513442 A | 5/2021 |
| KR | 20110032444 A | 3/2011 |
| KR | 101943440 B1 | 1/2019 |
| WO | 2012/035492 A1 | 3/2012 |
| WO | 2016/109886 A1 | 7/2016 |
| WO | 2019055681 A1 | 3/2019 |
| WO | 2020243285 A1 | 12/2020 |
| WO | 2021026231 A1 | 2/2021 |
| WO | 2021071540 A1 | 4/2021 |
| WO | 2021161162 A1 | 8/2021 |
| WO | 2021161184 A1 | 8/2021 |

OTHER PUBLICATIONS

"Plenary 1: Colubris MX"—YouTube Video link address https://www.youtube.com/watch?v=in_luQiAZg8 dated Aug. 20, 2020.

International Search Report and Written Opinion, of the Korean Intellectual Property Office, as ISA, mailed Apr. 6, 2023, in corresponding International Patent Application PCT/US2022/051217.

International Search Report and Written Opinion, of the Korean Intellectual Property Office, as ISA, mailed Apr. 6, 2023, in corresponding International Patent Application PCT/US2022/051220.

International Search Report and Written Opinion, of the Korean Intellectual Property Office, as ISA, mailed Apr. 7, 2023, in corresponding International Patent Application PCT/US2022/051225.

International Search Report and Written Opinion, of the Korean Intellectual Property Office, as ISA, mailed Apr. 6, 2023, in corresponding International Patent Application PCT/US2022/051237.

International Search Report and Written Opinion, of the Korean Intellectual Property Office, as ISA, mailed Apr. 6, 2023, in corresponding International Patent Application PCT/US2022/051246.

International Search Report and Written Opinion, of the Korean Intellectual Property Office, as ISA, mailed Apr. 6, 2023, in corresponding International Patent Application PCT/US2022/051255.

International Search Report and Written Opinion, of the Korean Intellectual Property Office, as ISA, mailed Apr. 6, 2023, in corresponding International Patent Application PCT/US2022/051259.

International Search Report and Written Opinion, of the Korean Intellectual Property Office, as ISA, mailed Apr. 6, 2023, in corresponding International Patent Application PCT/US2022/051261.

International Search Report and Written Opinion, of the Korean Intellectual Property Office, as ISA, mailed Apr. 14, 2023, in corresponding International Patent Application PCT/US2022/051265.

International Search Report and Written Opinion, of the Korean Intellectual Property Office, as ISA, mailed Apr. 6, 2023, in corresponding International Patent Application PCT/US2022/051262.

Extended European Search Report, dated Nov. 27, 2025, in corresponding European Patent Application No. 22902070.6.

* cited by examiner

100

100

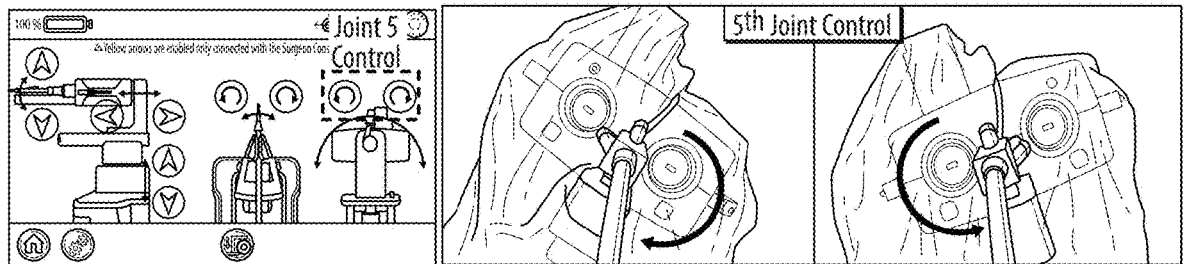
Fig. 12A                    Fig. 12B
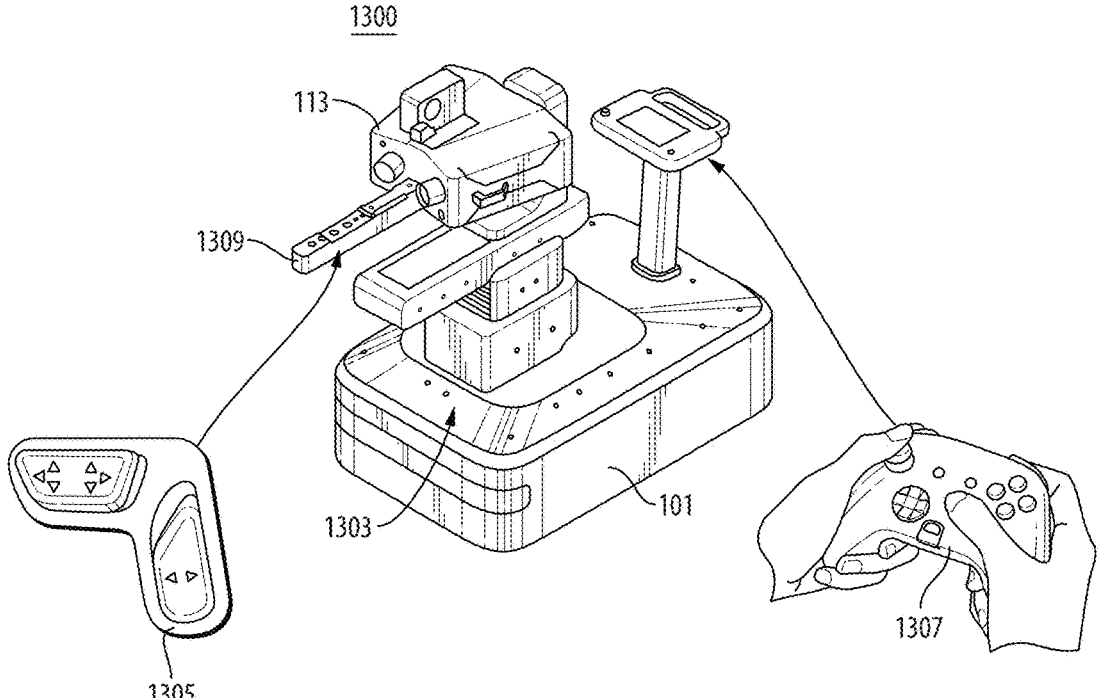
Fig. 13A

1305

1

POSITION CONTROL FOR PATIENT CONSOLE

CROSS-REFERENCE TO RELATED APPLICATIONS

This application is a continuation of International Patent Application No. PCT/US2022/051225 filed Nov. 29, 2022, which claims priority to and the benefit of U.S. Provisional Application No. 63/284,506, filed Nov. 30, 2021, the entire contents of which are herein incorporated by reference in their entirety.

FIELD

This disclosure relates to robotic surgical systems, e.g., for minimally invasive surgery including, but not limited to, endoluminal and single-site surgery.

BACKGROUND

Minimally invasive surgery such as endoluminal and single-site robotic surgery offer significant advantages versus traditional robotic surgery. For example, in endoluminal robotic surgery, no incision need be made to access difficult to access locations within a patient's natural lumen. This dramatically reduces and/or eliminates recovery time and improves procedural safety. A single-site system reduces incisions to a minimum single-site, which reduces an otherwise larger number of incisions to provide access for certain procedures.

Certain endoluminal and single-site robotic surgical systems have been proposed. Examples of such systems and related components can be found in U.S. Pat. No. 10,881,422, as well as U.S. Patent Application Nos. US20210322046, US20210322045, US20190117247, US20210275266, US20210267702, US20200107898, US20200397457, US202000397456, US20200315645, and US201962914226, all of the above being incorporated by reference herein in their entirety.

Conventional surgical robotics and systems have generally been considered satisfactory for their intended purpose. However, there is still a need in the art for improved robotic surgical systems, devices, methods, controls, and components, especially those configured for endoluminal and single-site surgery. The present disclosure provides improvements in such areas, for example.

SUMMARY

In accordance with at least one aspect of this disclosure, a patient console for a robotic surgical system can include a base, and a positioning assembly attached to the base and configured to position an instrument controller assembly. The positioning assembly includes a remote control device operatively connected to the positioning assembly to control movement of one or more portions of the positioning assembly such that a user is capable of having a direct line-of-sight of a patient when using the remote control device.

In certain embodiments, the remote control device can be configured to be mounted to or is mounted to an exterior of a portion of the instrument controller assembly and/or the base. For example, the remote control device can be removeably mounted to the instrument controller assembly and/or the base. In certain embodiments, the remote control device is configured to be mounted to or is mounted to an overtube arm of the instrument controller assembly. The overtube arm can be configured to receive and/or support an overtube thereon (e.g., to control a position of the overtube as shown and disclosed herein). In certain embodiments, the remote control device is wirelessly connected to the positioning assembly.

The control device can include a controller having one or more joysticks and/or one or more buttons. In certain embodiments, the control device can be configured control less than all portions of the positioning assembly.

In accordance with at least one aspect of this disclosure, a patient console for a robotic surgical system can include a base, and a positioning assembly attached to the base and configured to position an instrument controller assembly. The patient console can include the instrument controller assembly. A control device can be mounted to the instrument controller assembly and operatively connected to the positioning assembly to control movement of one or more portions of the positioning assembly such that a user is capable of having a direct line-of-sight of a patient when using the control device. The control device can be mounted and/or otherwise be similar to any suitable control device disclosed herein (e.g., as described above).

In accordance with at least one aspect of this disclosure, a robotic surgical system can include a patient console having a base and a positioning assembly attached to the base and configured to position an instrument controller assembly. The positioning assembly can be any suitable positioning assembly disclosed herein, e.g., as described above.

In accordance with at least one aspect of this disclosure, a method can include controlling movement of one or more portions of a positioning assembly attached to a base of a patient console using a remote control device operatively connected to the positioning assembly while maintaining a direct line-of-sight of a patient. In certain embodiments, controlling the movement of the one or more portions of the positioning assembly includes using the remote control device while the remote control device is mounted to an exterior of a portion of the instrument controller assembly. In certain embodiments, controlling the movement of the one or more portions of the positioning assembly includes using the remote control device while the remote control device is mounted to an overtube arm of the instrument controller assembly which has an overtube thereon. In certain embodiments, controlling the movement of the one or more portions of the positioning assembly includes using a controller having one or more joysticks and one or more buttons. In certain embodiments, controlling the movement of the one or more portions of the positioning assembly includes controlling less than all portions of the positioning assembly. In certain embodiments, the remote control device is wirelessly connected to the positioning assembly.

These and other features of the embodiments of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein:

FIGS. 12A and 12B illustrate a control the fifth joint, e.g., a roll rotation device;

FIG. 13A is a schematic perspective view of an embodiment of a patient console in accordance with this disclosure;

DETAILED DESCRIPTION

Figure 1:
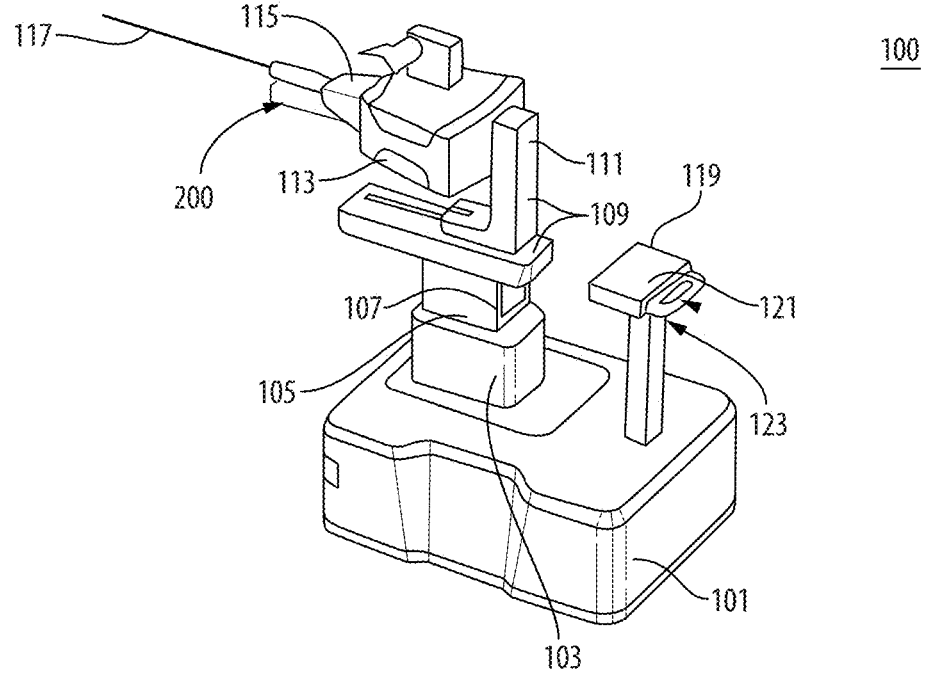
FIG. 1 is a perspective view of an embodiment of a patient console in accordance with this disclosure.

Reference will now be made to the drawings wherein like reference numerals identify similar structural features or aspects of the subject disclosure. For purposes of explanation and illustration, and not limitation, an illustrative view of an embodiment of a system in accordance with the disclosure is shown in FIG. 1 and is designated generally by reference character 100. Other embodiments and/or aspects of this disclosure are shown in FIGS. 2-14.

Referring to FIGS. 1-6 a patient console 100 (e.g., a cart) for a robotic surgical system can include a base 101 and a positioning arm 102. The positioning arm 102 includes a vertical lift 103 (e.g., joint J1) attached to a top of the base 101 and configured to provide up and down motion in a vertical axis A1. The patient console 100 can include a yaw rotation device 105 (e.g., joint J2) attached to the top of the vertical lift 103 and configured to provide a yaw rotation about the vertical axis A1. The patient console 100 can include a pitch rotation device 107 (e.g., joint J3) attached to the top of the yaw rotation device 105 to provide a pitch rotation about a pitch axis A2 orthogonal to the vertical axis A1. The patient console 100 can include a translation device 109 (e.g., joint J4) attached to the top of the pitch rotation device 107 and configured to provide sliding translation along a translation axis A3. The patient console 100 can include a roll rotation device 111 (e.g., joint J5) attached to the translation device 109 to roll relative to the translation device 109 about a roll axis A4 to provide a roll to an instrument controller assembly 113.

An angle of the translation axis A3 and the roll axis A4 relative to horizontal can be a function of the pitch rotation provided by the pitch rotation device 107. A direction of the translation axis A3 and the roll axis A4 can be a function of the yaw rotation provided by the yaw rotation device 105.

The console 100 can include an instrument controller 113 assembly connected to the roll rotation device 111, the instrument controller assembly 113 including one or more instrument controllers 115 for controlling a medical device (not shown) for performing a surgical operation. The vertical lift 103, the yaw rotation device 105, the pitch rotation device 107, the translation device 109, and the roll rotation device 111 can provide 5-degrees of freedom to the instrument controller assembly 113 (and thus the overtube 117 mounted thereon), for example. In certain embodiments, the base 101 can be configured to move relative to a floor to provide an additional degree of freedom of motion.

The patient console 100 can be configured to allow for positioning of a medical device for a transanal procedure, a transoral procedure, or a transvaginal procedure. Any other suitable procedure is contemplated herein.

Figure 7:
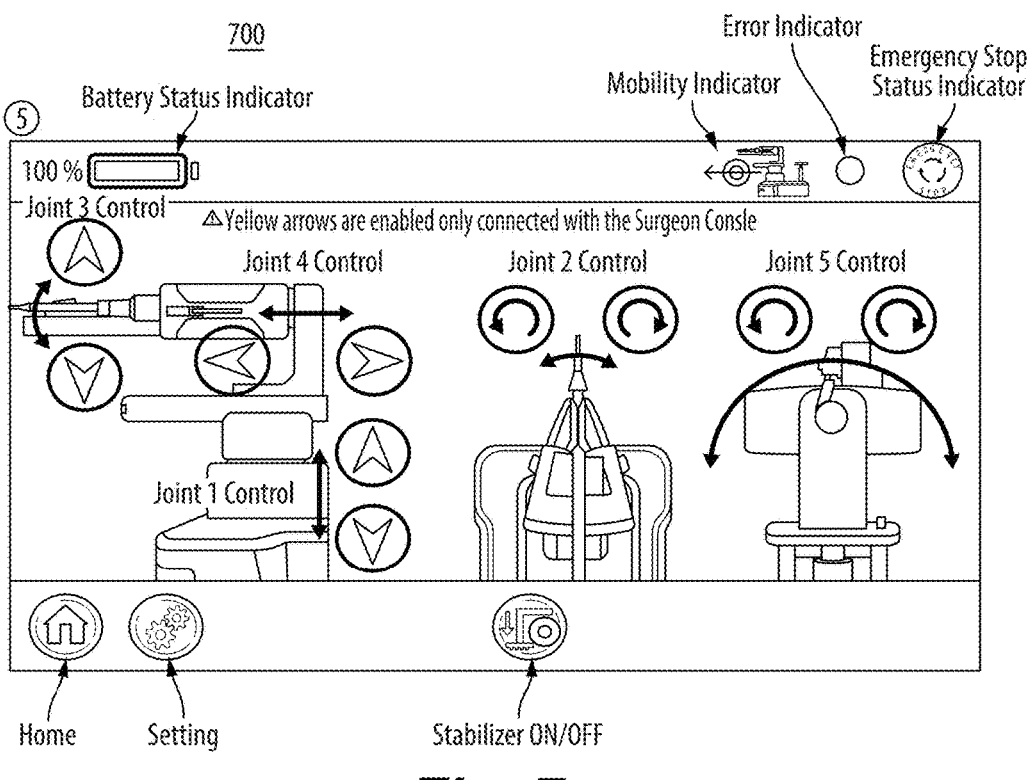
FIG. 7 shows an embodiment of a graphical user interface (GUI) for an embodiment of a user input device of the patient console.

The console 100 can include a user input device 119 attached to the base 101 and configured to control each of the vertical lift 103, the yaw rotation device 105, the pitch rotation device 107, the translation device 109, and the roll rotation device 111. Referring additionally to FIG. 7, the user input device 119 can include a display 121 (e.g., a touchscreen) having a graphical user interface (GUI) 700 for controlling each of the vertical lift 103, the yaw rotation device 105, the pitch rotation device 107, the translation device 109, and the roll rotation device 111. As shown, the GUI 700 can be configured to indicate an orientation and position of the instrument controller assembly 113 from one or more angles. The GUI 700 can be configured to have any suitable digital buttons, inputs, indicators, images, text, and/or other content (e.g., arrow buttons indicating the direction of rotation as shown and/or any other indicators and/or control buttons.

In certain embodiments, one or more of the vertical lift 103, the yaw rotation device 105, the pitch rotation device 107, the translation device 109, and the roll rotation device 111 can be controlled by a remote surgeon console in addition to the user input device 119, for example. In certain embodiments, the user input device 119 can control all of the vertical lift 103, the yaw rotation device 105, the pitch rotation device 107, the translation device 109, and the roll rotation device 111, and a remote surgeon console can control the translation device 109 and the roll rotation device 111 only.

Figure 2:
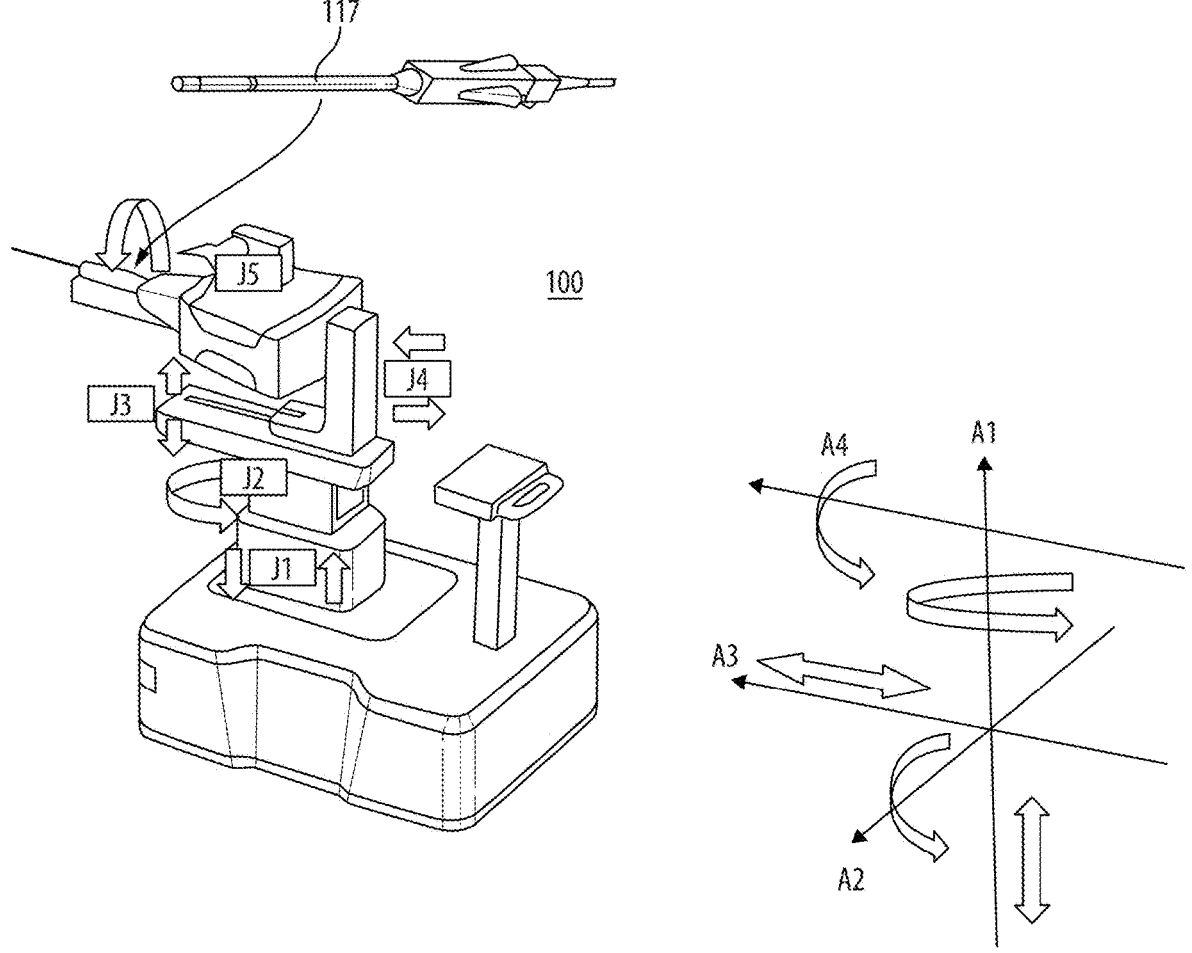
FIG. 2 is a schematic view of the embodiment of FIG. 1, showing five degrees of freedom at five joints.
Figure 2A:
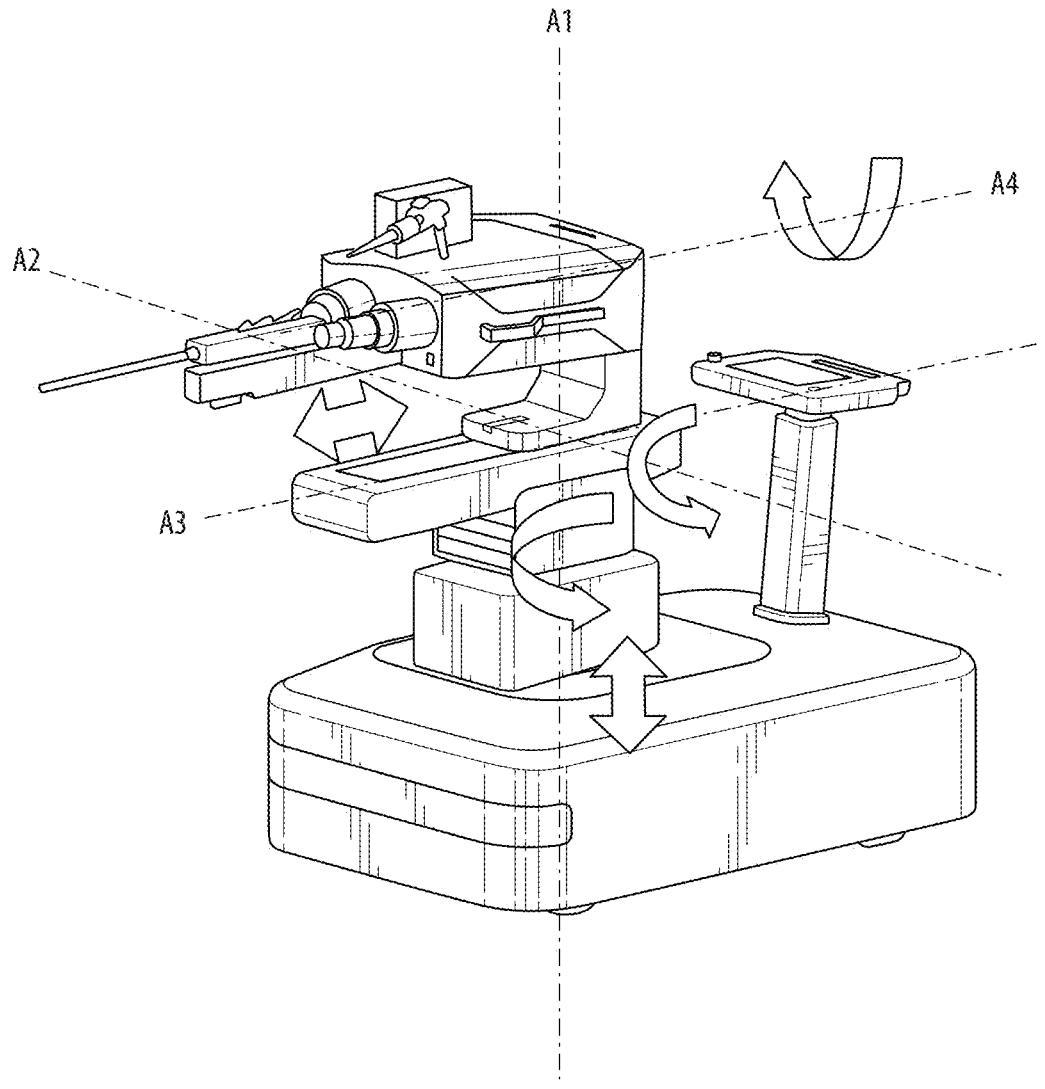
FIG. 2A is a schematic view of the embodiment as shown in FIG. 2, illustrating axes of motion (e.g., A1, A2, A3, and A4)
Figure 3:
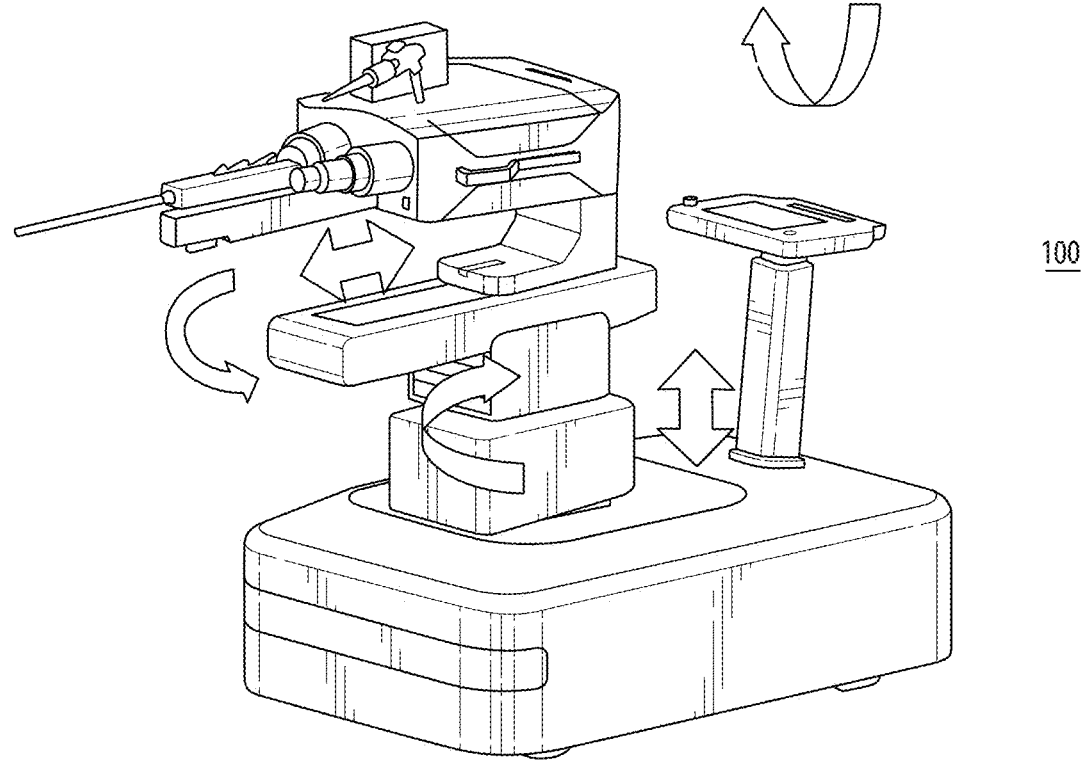
FIG. 3 is another view of the embodiment of FIG. 2, showing the five degrees of freedom.
Figure 4:
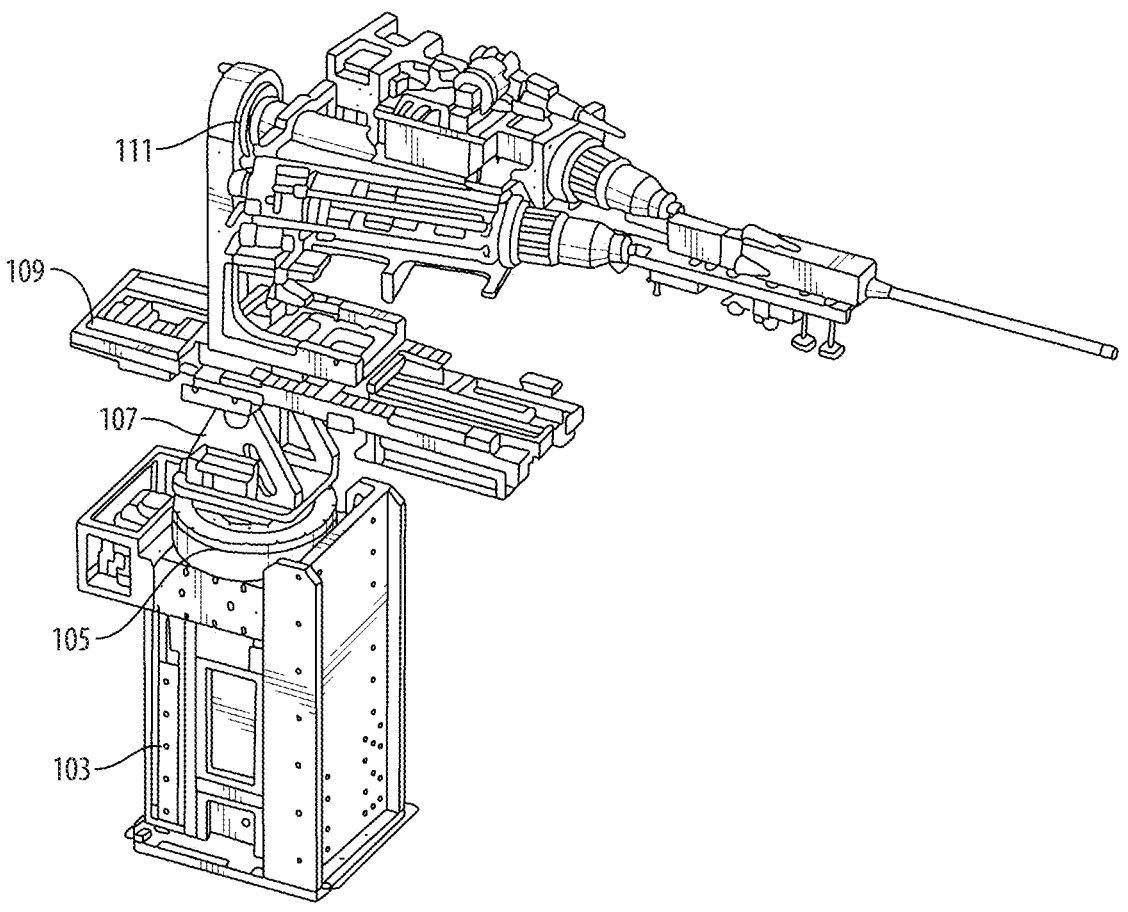
FIG. 4 is an elevation view of the embodiment of FIG. 1, showing in a storage position.
Figure 5:
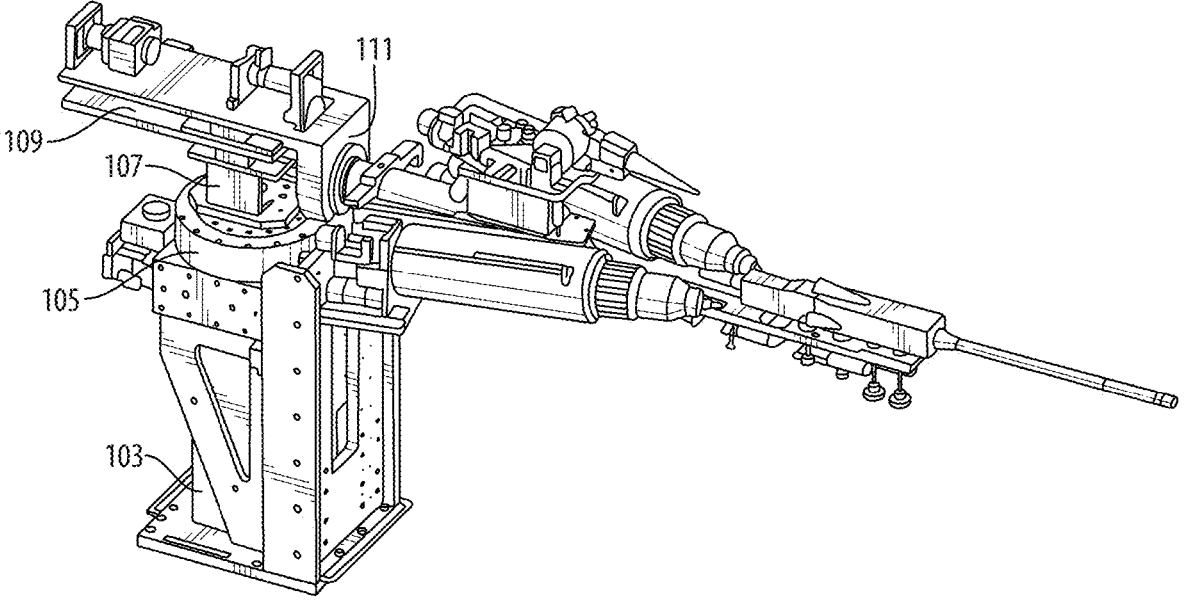
FIG. 5 is a perspective view of the embodiment of FIG. 1, showing the positioning components and with the base and outer housing removed.
Figure 6:
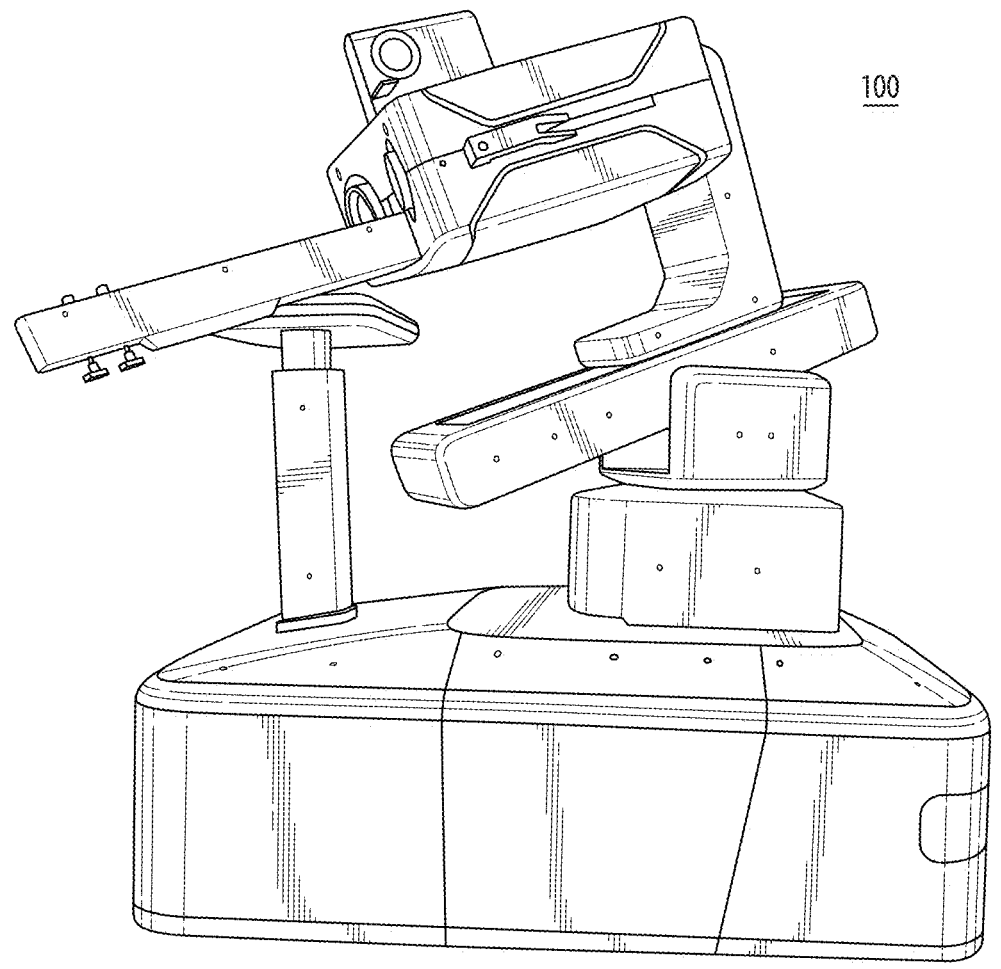
FIG. 6 is a perspective view of another embodiment of the positioning components of a patient console and with the base and outer housing removed.
Figure 8A:
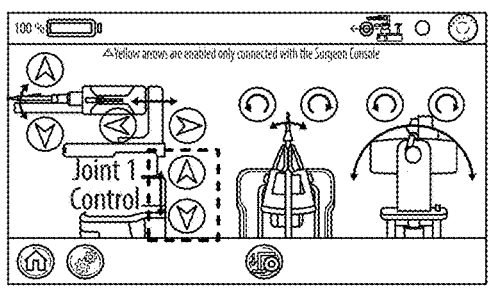
FIGS. 8A and 8B illustrate a control the first joint, e.g., a vertical lift as shown.
Figure 8B:
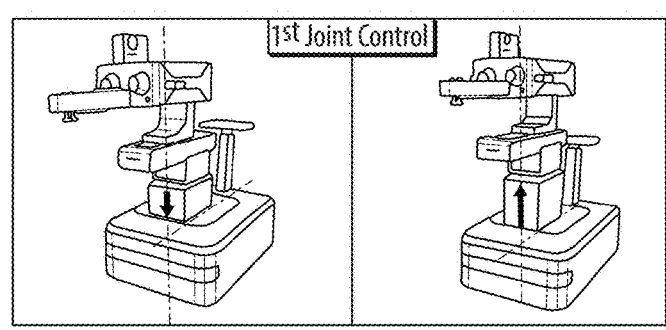
Figure 9A:
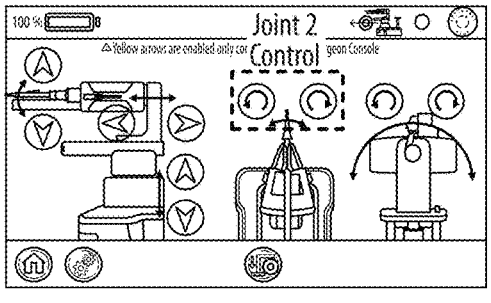
FIGS. 9A and 9B illustrate a control the second joint, e.g., a yaw rotation device as shown.
Figure 9B:
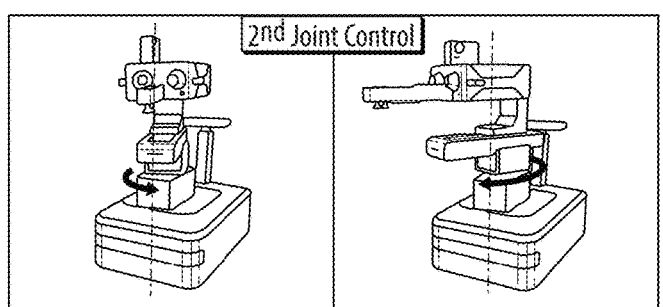
Figure 10A:
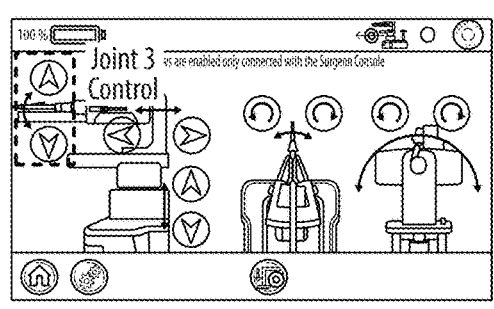
FIGS. 10A and 10B illustrate a control the third joint, e.g., a pitch rotation device as shown.
Figure 10B:
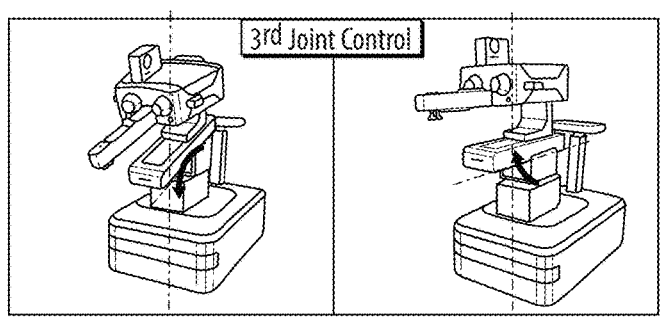
Figure 11A:
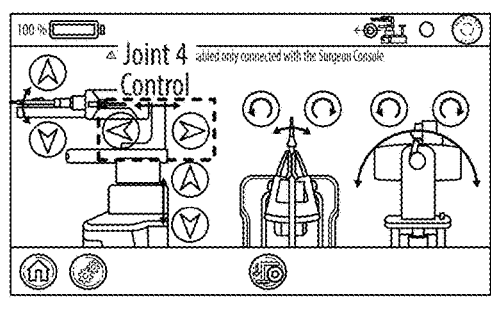
FIGS. 11A and 11B illustrate a control the fourth joint, e.g., a translation device as shown.
Figure 11B:
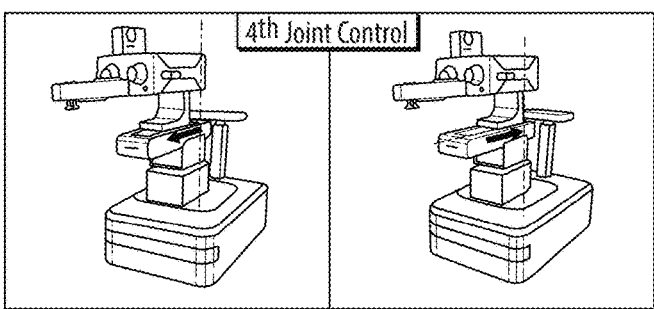

FIG. 1 is a perspective view of an embodiment of a patient console in accordance with this disclosure. FIG. 2 is a schematic view of the embodiment of FIG. 1, showing five degrees of freedom at five joints (e.g., J1, J2, J3, J4, J5). FIG. 3 is another view of the embodiment of FIG. 2, showing the five degrees of freedom. FIG. 4 is an elevation view of the embodiment of FIG. 1, showing in a storage position. FIG. 5 is a perspective view of the embodiment of FIG. 1, showing the positioning components and with the base and outer housing removed. FIG. 6 is a perspective view of another embodiment of the positioning components of a patient console and with the base and outer housing removed. FIG. 7 shows an embodiment of a graphical user interface (GUI) for an embodiment of a user input device of the patient console. FIGS. 8A and 8B illustrate a control the first joint (e.g., J1 as shown in FIG. 2), e.g., a vertical lift as shown. FIGS. 9A and 9B illustrate a control the second joint (e.g., J2 as shown in FIG. 2), e.g., a yaw rotation device as shown. FIGS. 10A and 10B illustrate a control the third joint (e.g., J3 as shown in FIG. 2), e.g., a pitch rotation device as shown. FIGS. 11A and 11B illustrate a control the fourth joint (e.g., J4 as shown in FIG. 2), e.g., a translation device as shown. FIGS. 12A and 12B illustrate a control the fifth joint (e.g., J5 as shown in FIG. 2), e.g., a roll rotation device.

Embodiments can be used for robotic surgical systems, for example. Any suitable uses and/or embodiments for use are contemplated herein.

Embodiments include five degree of freedom positioning patient console 100 (e.g., a patient cart). Embodiments can include an advantageous order of stacking of the degrees of freedom.

Embodiments can provide movements for the position of the overtube 117 attached to the overtube arm 200. Embodiments can include five joints and each joint provides specific motion. In certain embodiments, joint 1 can provides up/down motion within 0-400 mm. In certain embodiments, joint 2 can provide rotation motion within −90-+150 degrees. In certain embodiments, joint 3 can provide tilting motion within 0-35 degrees downwards. In certain embodiments, joint 4 can provide translation motion within 0-400 mm. In certain embodiments, joint 5 can provide rolling motion within −170-+170 degrees.

In certain embodiments, all the joints can be controlled by a nurse using the touchscreen on the patient console 100. Joint 4 and Joint 5 can be controlled by a surgeon by using the hand control devices and overtube pedal on the surgeon console (not shown).

Certain embodiments can include an interface (e.g. user input device 119) that has a touchscreen (e.g. the display 121), a base cart handle 123, and stabilizer. Certain embodiments can allow control of the mobility of the patient console 100 system with drive control switches and the direction of force applied on the base cart handle 123. Certain embodiments can allow control via the base cart handle 123 is activated only when the drive control switches are pressed down halfway and held. Certain embodiments can be immobilized by activating the stabilizers via a touchscreen to prevent unwanted movement during surgery.

Embodiments of a user input device 119 can be used to control the positioning arm 102 and patient console 100. Embodiments of a user input device can indicate the status of the patient console 100. Embodiments of a user input device 119 can provide a setting menu for the base cart and its touchscreen. Embodiments of a user input device can display buttons to control movements of the positioning arm 102.

Embodiments of a touchscreen GUI 700 can include a loading user interface that displays immediately when the power is on and initializes the patient console 100 and touchscreen. The GUI can include a home screen that provides access menu buttons to the Pose Setting, Patient Cart, and Diagnosis, for example. Embodiments of a GUI 700 can include a Patient Cart Setting Screen that provides detailed settings of the patient console 100 to adjust values related to mobility. The GUI 700 can include a Setting Screen that provides a setting menu to adjust the brightness of the touch screen. The GUI 700 can include a pose setting screen that provides touch buttons to adjust the pose setting of each joint of the positioning arm 102. In FIG. 7, various modes of exemplary indicators are provided in the GUI 700. Embodiments of a GUI can include a mobility indicator that shows whether the patient console 100 can be moved or not.

Embodiments can include an error indicator that shows normal or abnormal status of the system with two colors of green and orange. If the error is occurred, orange color can be showing.

An emergency stop indicator can show activation of the emergency stop. When the emergency stop is activated, the icon can be changed to orange and red colors. Embodiments can include a home button that can provides function to return to the home screen. Embodiments can include a setting button that provides a function to activate a setting menu. Embodiments can include a stabilizer on/off button that provides a function to activate/deactivate the stabilizer of the patient console 100.

In certain embodiments, a user can move the positioning arm 102 to the required target region by using the positioning arm 102 touchscreen controls. A user can insert the overtube 117 into the patient, and then move the positioning arm to align with the overtube 117. A user can then connect the overtube 117 to the overtube arm 200 and tighten the knobs.

The user can control the positioning arm 102 using the touchscreen controls provided on the patient console 100. The user can push the buttons provided on the touchscreen to move each joint of the positioning arm 102. The positioning arm 102 can provide five degrees of freedom of motion. A user can press and hold the button shown on the touchscreen to move the joint in the specified direction. The user can release the touchscreen button to stop moving the positioning arm 102. Table 1 shows an embodiment of motions provided by each joint J1-J5.

TABLE 1

| Joint | Motion Direction | Motion Direction |
|-------|-----------------|------------------|
| J1 | Up | Down |
| J2 | Right | Left |
| J3 | Head Up | Head Down |
| J4 | Backward | Forward |
| J5 | Counterclockwise | Clockwise |

In certain embodiments, a surgeon can control the positioning arm 102 Joints 4 and 5 using hand control device along with an overtube pedal on a surgeon console. Any suitable other control scheme is contemplated herein.

Referring to FIG. 13A, in accordance with at least one aspect of this disclosure, a patient console 1300 for a robotic surgical system can include a base 101, and a positioning assembly 1303 attached to the base 101 and configured to position an instrument controller assembly 113. The positioning assembly 1303 can be the same as that disclosed above with respect to the embodiment of FIG. 1, for example (e.g., including 5 degrees of freedom and associated rotation, lift, and translation devices). However, and other suitable positioning assembly is contemplated herein.

The positioning assembly 1303 can include a remote control device 1305, 1307 (either being wireless or wired) operatively connected to the positioning assembly 1303 (e.g., directly or indirectly) to control movement of one or more portions (e.g., one or more rotation, lift, and/or translation devices) of the positioning assembly 1303 such that a user is capable of having a direct line-of-sight of a patient when using the remote control device 1305, 1307. In certain embodiments, the remote control device 1305, 1307 can be wireless (e.g., connected to a user input device 119 that has a position control module for the positioning assembly 1303, otherwise connected to a position control module that controls motion of the positioning assembly 1303 as a function of inputs, or connected to directly control one or more portions of the positioning assembly 1303) such that it is wirelessly connected to the positioning assembly. In certain embodiments, the base 101 (e.g., one or more motorized wheels) can be controlled by the remote control device 1305, 1307.

Figure 13B:
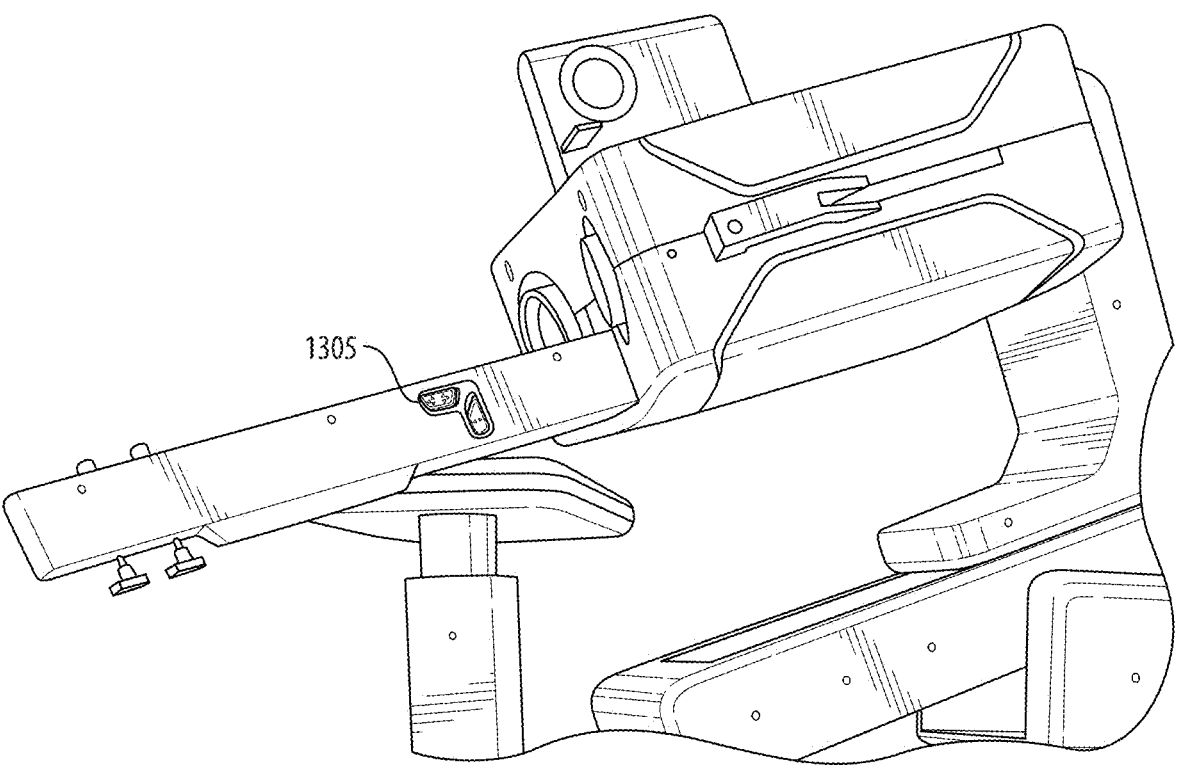
FIG. 13B is a partial elevation view of the embodiment of FIG. 13A.

In certain embodiments, the remote control device 1305 can be configured to be mounted to or is mounted to an exterior of a portion of the instrument controller assembly 113 as shown in FIG. 13B. For example, the control device 1305 can be removeably mounted to the instrument controller assembly 113 (e.g., via one or more magnets). However, it is contemplated that the control device 1305 may be fixed to the instrument controller assembly 113 as it can be within a surgical drape in use based on its location on the instrument controller assembly 113 (e.g., on an overtube arm). It is contemplated that multiple remote control devices can be utilized in various locations. Each can have a control priority such that control of a higher priority device overrides any accidental control from a lower priority device.

Figure 13C:
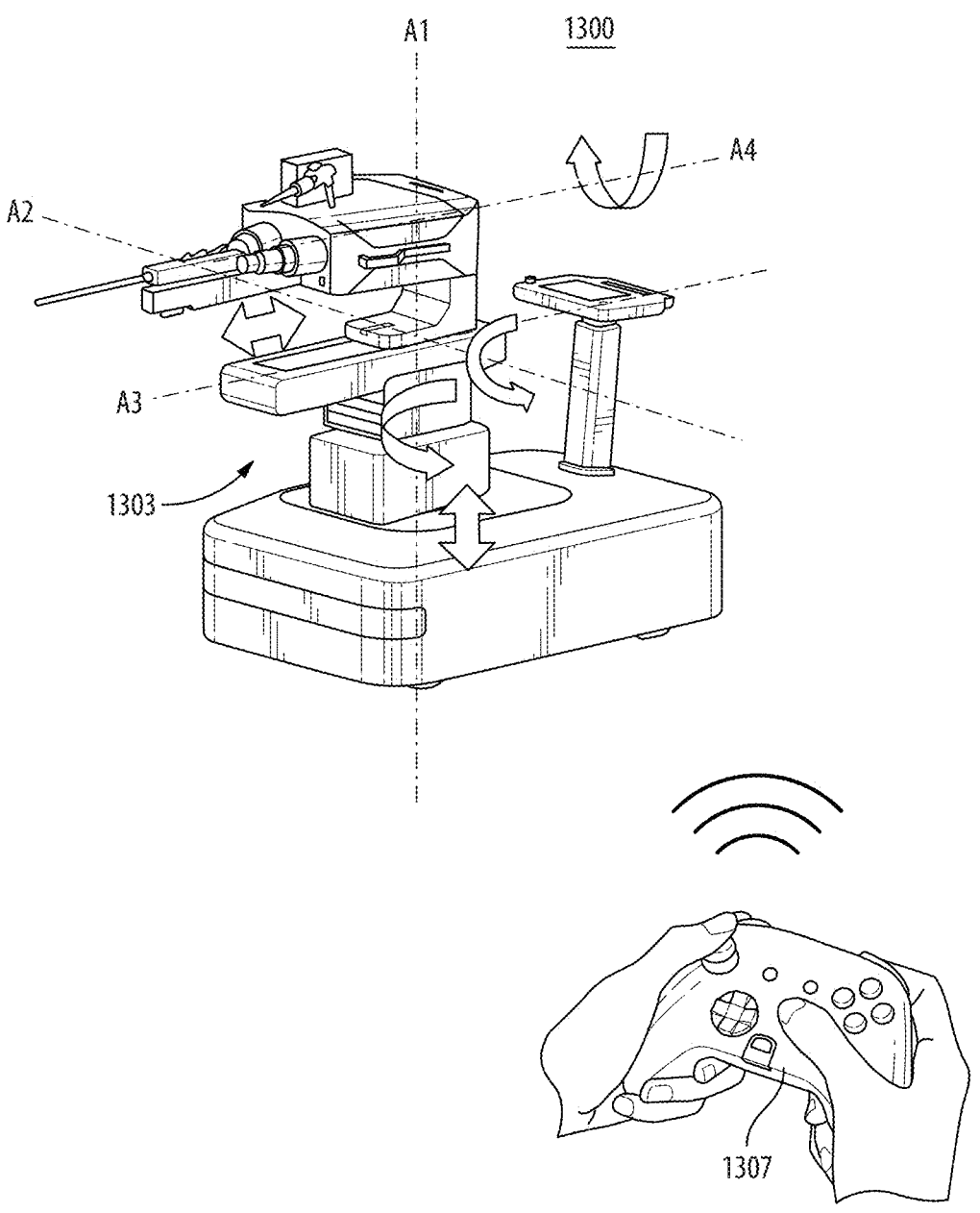
FIG. 13C is a schematic perspective view of the embodiment of FIG. 13A, shown being controlled remotely with a controller.

In certain embodiments, the remote control device 1305 is configured to be mounted to or is mounted to an overtube arm 1309 of the instrument controller assembly 113. The overtube arm 1309 can be configured to receive and/or support an overtube 117 thereon (e.g., to control a position of the overtube as shown and disclosed herein). The overtube arm 1309 can house motors for driving one or more overtube steering devices (e.g., cables). As shown in FIG. 13C, mounting a remote (e.g., wireless or wired) control device 1305 to the overtube arm 1309 allows a user to be in front of the base 101 and to have a direct line of sight of the patient so as to be able to accurately and quickly position the patient console 1300 and overtube 117 relative to a patient. Any other suitable location to mount a remote control device 1305 is contemplated herein.

The remote control device 1307 can include a controller (e.g., a dual joystick video game controller as shown) having one or more joysticks and one or more buttons. However, any suitable input device (e.g., buttons only as shown on remote device 1305, a touch screen, any combination thereof) is contemplated herein. In certain embodiments, the user input device 119 (e.g., with touch screen input) can be wireless and detachable from a base steering post 1311 such that the user input device 119 can be the remote control device 1307.

In certain embodiments, the remote control device 1305, 1307 can be configured control less than all portions of the positioning assembly 1303. For example, the remote control device 1305 mounted to the overtube arm 1309 may be configured to only operate in the translation axis A3 and the vertical axis A1. However, the remote control device 1305, 1307 can be configured to operate any suitable portions (e.g., all or any other suitable combination of portions) of the positioning assembly 1303 and/or the base 101 (e.g., to control wheels) are contemplated herein (e.g., all the same functions as the user input device 119).

Embodiments can include a remote controller can be used by an assistant to adjust and position the patient console 1300 for docking, for example. In certain embodiments, user-friendly levers/buttons can be integrated into the positioning assembly 1303 and/or the instrument assembly 113 for the assistant to use. For example, certain embodiments include an interface that has levers and/or buttons on an overtube arm 1309 or a remote control that can be used.

Figure 14:
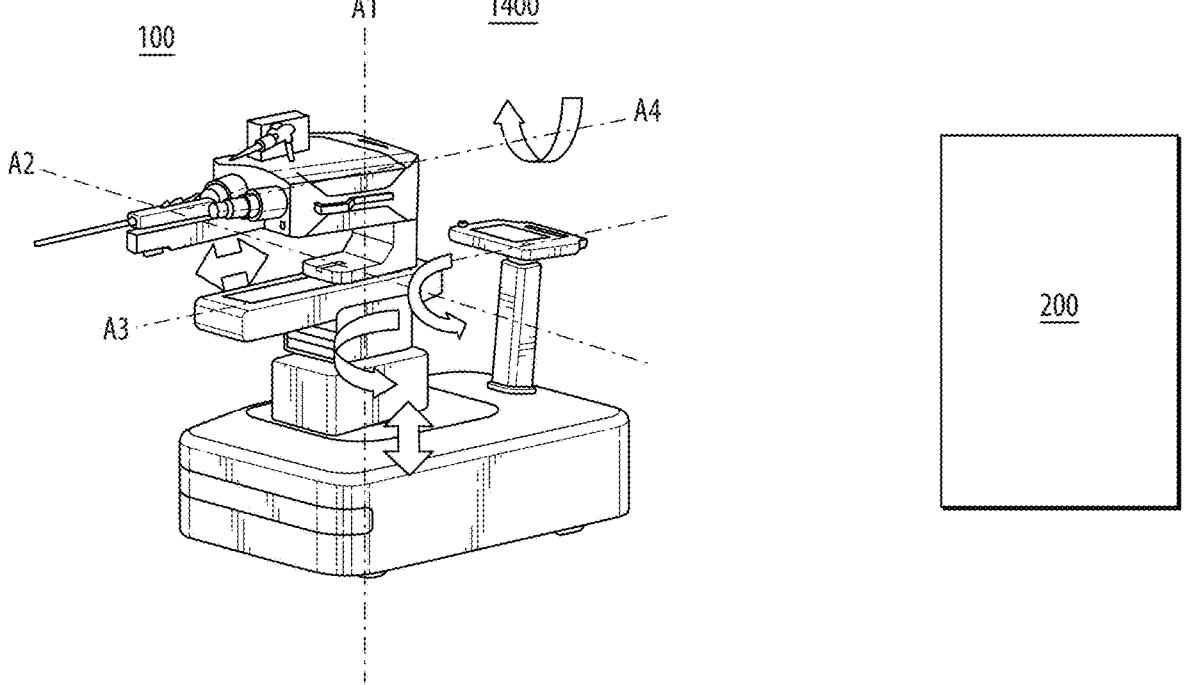
FIG. 14 illustrates an embodiment of a robotic surgical system in accordance with this disclosure.

In accordance with at least one aspect of this disclosure, referring to FIG. 14, a robotic surgical system 1400 can include a patient console 100, 1300 having a base and a positioning assembly 1303. The patient console 100 and positioning assembly 1303 can be any suitable embodiment disclosed herein, e.g., console 100, 1300 as described above, for example. The robotic surgical system 1400 can include a surgeon console 200 configured to allow a surgeon to remotely operate one or more controllers connected to the patient console 100, 1300 (e.g., wirelessly or via a wired connection) to perform robotic surgery or other suitable medical procedure. Any suitable surgeon console 200 and/or control inputs are contemplated herein. In certain embodiments, the surgeon console 200 can be configured to allow control of one or more of the vertical lift 103, the yaw rotation device 105, the pitch rotation device 107, the translation device 109, and the roll rotation device 111 for positioning the medical instrument attached to the patient console 100 in situ. For example, the roll rotation device 111 can be configured to be operated by one or more hand controls of the surgeon console 200 to allow rotation of the overtube 117 (which contains one or more medical instruments and/or camera) about axis A4 to rotate the distal end of the medical device(s), camera, and/or overtube 117 in situ.

In accordance with at least one aspect of this disclosure, a method for performing a robotic medical procedure can include using a vertical lift 103 attached to a top of a base of a patient console to provide up and down motion in a vertical axis A1, using a yaw rotation device 105 attached to the top of the vertical lift 103 to provide a yaw rotation about the vertical axis A1, using a pitch rotation device 107 attached to the top of the yaw rotation device 105 and configured to provide a pitch rotation about a pitch axis A2 orthogonal to the vertical axis A1, using a translation device 109 attached to the top of the pitch rotation device 107 and configured to provide sliding translation along a translation axis A3, and using a roll rotation device 111 attached to the translation device 109 to roll relative to the translation device 109 about a roll axis A4 to provide a roll to an instrument controller assembly 113. An angle of the translation axis A3 and the roll axis A4 relative to horizontal can be a function of the pitch rotation provided by the pitch rotation device 107 (about axis A2). A direction of the translation axis A3 and the roll axis A4 can be a function of the yaw rotation about the vertical axis A1 provided by the yaw rotation device 105.

The method can include using an instrument controller assembly 113 having one or more instrument controllers 115 connected to the roll rotation device 111 for controlling a medical device for performing a surgical operation, and using the vertical lift 103, the yaw rotation device 105, the pitch rotation device 107, the translation device 109, and the roll rotation device 111 provide 5-degrees of freedom to the instrument controller assembly 113. The method can include moving the base of the patient console 100 relative to a floor (on which the patient console 100 is standing) to provide an additional degree of freedom of motion. The method can include positioning a medical device for a transanal procedure, a transoral procedure, or a transvaginal procedure.

The method can include controlling each of the vertical lift 103, the yaw rotation device 105, the pitch rotation device 107, the translation device 109, and the roll rotation device 111 with a user input device. The method can include using a graphical user interface (GUI) 700 to control each of the vertical lift 103, the yaw rotation device 105, the pitch rotation device 107, the translation device 109, and the roll rotation device 111. The method can include any other suitable method(s) and/or portion(s) thereof.

In accordance with at least one aspect of this disclosure, a method can include controlling movement of one or more portions of a positioning assembly 1303 attached to a base 101 of a patient console 1300 using a remote control device 1305 and/or 1307 operatively connected to the positioning assembly 1303 and/or base 1307 while maintaining a direct line-of-sight of a patient (e.g., on a surgical table). In certain embodiments, controlling the movement of the one or more portions of the positioning assembly 1303 can include using the remote control device 1305 while the remote control device 1305 is mounted to an exterior of a portion of an instrument controller assembly 113 and/or base 101. In certain embodiments, controlling the movement of the one or more portions of the positioning assembly 1303 can include using the remote control device 1305 while the remote control device is mounted to an overtube arm 1309 of the instrument controller assembly 113 (e.g., which has an overtube mounted thereon during a medical procedure). In such embodiments, the overtube arm 1309 can be draped during use and inside the sterile zone such that a user presses on the drape to operate the remote control device 1305 (e.g., which can have one or more push buttons). In this way, the remote control device 1305 remains sterile and the sterile zone remains intact.

In certain embodiments, controlling the movement of the one or more portions of the positioning assembly 1303 can include using a controller 1307 having one or more joysticks and/or one or more buttons (e.g., a videogame controller as shown). However, any other suitable control structure for controlling movement of the base 101 and/or positioning assembly 1303 is contemplated herein. For example, the remote control device 1307 can be a removeable touch screen (e.g., shown on a pedestal attached to the base 101) which can be wirelessly connected to or wired to the base 101 to control the base 101 and/or the positioning assembly 1303 remotely from the system 1300. In certain embodiments, the removeable touch screen can include one or more joysticks and/or physical buttons, for example.

In certain embodiments, controlling the movement of the one or more portions of the positioning assembly 1303 can include controlling less than all portions of the positioning assembly 1303. For example, the controls on the remote control device 1305, 1307 can be limited to one or more axes of control to limit erroneous movement and for patient safety. For example, the remote control device 1305 can be configured to provide only movements in a forward and backward axis, and/or and up and down axis for general positioning of an overtube.

As will be appreciated by those skilled in the art, aspects of the present disclosure may be embodied as a system, method or computer program product. Accordingly, aspects of this disclosure may take the form of an entirely hardware embodiment, an entirely software embodiment (including firmware, resident software, micro-code, etc.), or an embodiment combining software and hardware aspects, all possibilities of which can be referred to herein as a "circuit," "module," or "system." A "circuit," "module," or "system" can include one or more portions of one or more separate physical hardware and/or software components that can together perform the disclosed function of the "circuit," "module," or "system", or a "circuit," "module," or "system" can be a single self-contained unit (e.g., of hardware and/or software). Furthermore, aspects of this disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of this disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of this disclosure may be described above with reference to flowchart illustrations and/or block diagrams of methods, apparatus (systems) and computer program products according to embodiments of this disclosure. It will be understood that each block of any flowchart illustrations and/or block diagrams, and combinations of blocks in any flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in any flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

Those having ordinary skill in the art understand that any numerical values disclosed herein can be exact values or can be values within a range. Further, any terms of approximation (e.g., "about", "approximately", "around") used in this disclosure can mean the stated value within a range. For example, in certain embodiments, the range can be within (plus or minus) 20%, or within 10%, or within 5%, or within 2%, or within any other suitable percentage or number as appreciated by those having ordinary skill in the art (e.g., for known tolerance limits or error ranges).

The articles "a", "an", and "the" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

Any suitable combination(s) of any disclosed embodiments and/or any suitable portion(s) thereof are contemplated herein as appreciated by those having ordinary skill in the art in view of this disclosure.

The embodiments of the present disclosure, as described above and shown in the drawings, provide for improvement in the art to which they pertain. While the subject disclosure includes reference to certain embodiments, those skilled in the art will readily appreciate that changes and/or modifications may be made thereto without departing from the spirit and scope of the subject disclosure.

What is claimed is:

1. A patient console for a robotic surgical system, comprising:
   a base;
   a positioning assembly attached to the base and configured to position an instrument controller assembly;
   the instrument controller assembly, attached to and supported by the positioning assembly; and
   a remote control device operatively connected to the positioning assembly to control movement of one or more portions of the positioning assembly such that a user is capable of having a direct line-of-sight of a patient when using the control device,
   wherein the positioning assembly comprises:
       a vertical lift device configured to provide up and down motion along a vertical axis;
       a pitch rotation device configured to provide a pitch rotation about a pitch axis orthogonal to the vertical axis;
       a translation device configured to provide sliding translation along a translation axis; and
       a roll rotation device to rotate about a roll axis to provide a roll to an instrument controller assembly, and
   wherein an angle of the translation axis and the roll axis relative to horizontal is a function of the pitch rotation provided by the pitch rotation device.

2. The patient console of claim 1, wherein the remote control device is configured to be mounted to or is mounted to an exterior of a portion of the instrument controller assembly and/or the base.

3. The patient console of claim 2, wherein the remote control device is removeably mounted to the instrument controller assembly and/or the base.

4. The patient console of claim 1, wherein the remote control device is configured to be mounted to or is mounted to an overtube arm of the instrument controller assembly, wherein the overtube arm is configured to receive and/or support an overtube thereon.

5. The patient console of claim 1, wherein the remote control device includes a controller having one or more joysticks and/or one or more buttons adapted and configured to control movement of respective portions of the positioning assembly upon manipulation by a user.

6. The patient console of claim 1, wherein the remote control device is configured to control fewer than all controllable portions of the positioning assembly.

7. The patient console of claim 1, wherein the remote control device is wirelessly connected to the positioning assembly.

8. The patient console of claim 1, wherein the instrument controller assembly comprises a plurality of instrument controllers configured and adapted to engage and drive robotic surgical instruments, and to engage an overtube arm.

9. The patient console of claim 8, wherein the overtube arm is adapted to engage and maintain the overtube in a fixed position relative to the instrument controller assembly.

10. The patient console of claim 8, wherein the instrument controller assembly comprises an overtube controller adapted and configured to engage and mechanically steer a steerable portion of an overtube.

11. A robotic surgical system, comprising:
  a patient console, comprising:
    a base;
    a positioning assembly attached to the base and configured to position an instrument controller assembly;
    a remote control device operatively connected to the positioning assembly to control movement of one or more portions of the positioning assembly prior to engagement of the instrument controller assembly with an overtube, such that a user is capable of having a direct line-of-sight of a patient when using the remote control device; and
    a physician console operatively connected to the patient console, adapted and configured to control movement of one or more portions of the positioning assembly after engagement of the instrument controller assembly with the overtube,
    wherein control of the positioning assembly by the surgeon console is limited to roll and linear translation portions thereof.

12. The robotic surgical system of claim 11, wherein the remote control device is configured to be mounted to or is mounted to an exterior of a portion of the instrument controller assembly and/or the base.

13. The robotic surgical system of claim 11, wherein the remote control device is configured to be mounted to or is mounted to an overtube arm of the instrument controller assembly, and wherein the overtube arm is configured to receive and/or support an overtube thereon.

14. The robotic surgical system of claim 11, wherein the remote control device is configured to control fewer than all controllable portions of the positioning assembly.

15. The robotic surgical system of claim 11, wherein the remote control device is wirelessly connected to the positioning assembly.

16. A method of controlling a positioning assembly, comprising:
  controlling movement of one or more portions of the positioning assembly attached to a base of a patient console using a remote control device operatively connected to the positioning assembly while maintaining a direct line-of-sight of a patient,
  wherein controlling the movement of the one or more portions of the positioning assembly includes using the remote control device while the remote control device is mounted to an exterior of a portion of the instrument controller assembly and/or the base,
  wherein controlling the movement of the one or more portions of the positioning assembly includes using the remote control device while the remote control device is mounted to an overtube arm of the instrument controller assembly which has an overtube thereon.

17. The method of claim 16, wherein controlling the movement of the one or more portions of the positioning assembly includes controlling fewer than all controllable portions of the positioning assembly.

* * * * *